(12) United States Patent
Huffman

(10) Patent No.: US 7,210,931 B1
(45) Date of Patent: May 1, 2007

(54) DENTAL MODEL BASE ASSEMBLY

(75) Inventor: Ronald E. Huffman, 725 Country Wood Way, Sapulpa, OK (US) 74066

(73) Assignee: Ronald E. Huffman, Oro Valley, AZ (US)

( * ) Notice: Subject to any disclaimer, the term of this patent is extended or adjusted under 35 U.S.C. 154(b) by 0 days.

(21) Appl. No.: 09/349,192

(22) Filed: Jul. 7, 1999

(51) Int. Cl.
*A61C 11/00* (2006.01)

(52) U.S. Cl. .............................. 433/60; 433/54; 433/57
(58) Field of Classification Search ................... 433/54, 433/57, 60, 64
See application file for complete search history.

(56) References Cited

U.S. PATENT DOCUMENTS

| | | | |
|---|---|---|---|
| 1,745,570 A | 2/1930 | Dimelow | |
| 1,780,117 A | 10/1930 | Craigo | |
| 2,398,671 A | 4/1946 | Saffir | |
| 2,585,857 A | 2/1952 | Schwartz | |
| 3,453,736 A | 7/1969 | Waltke | |
| 3,510,947 A | * 5/1970 | Tuccillo | 433/60 |
| 3,518,761 A | 7/1970 | Susman et al. | |
| 3,581,398 A | 6/1971 | Thomas | |
| 3,937,773 A | 2/1976 | Huffman | |
| 3,969,820 A | 7/1976 | Kulig et al. | |
| 4,022,419 A | 5/1977 | Haker | |
| 4,116,416 A | 9/1978 | Segura | |
| 4,122,606 A | 10/1978 | Roman | |
| 4,127,939 A | 12/1978 | Samuel et al. | |
| 4,203,219 A | 5/1980 | Wiener | |
| 4,242,812 A | 1/1981 | Randoll et al. | |
| 4,283,173 A | 8/1981 | Browne et al. | |
| 4,319,875 A | * 3/1982 | Beckwith | 433/60 |
| 4,371,339 A | 2/1983 | Zeiser | |
| 4,382,787 A | 5/1983 | Huffman | |
| 4,398,884 A | 8/1983 | Huffman | |
| 4,439,151 A | 3/1984 | Whelan | |
| 4,443,192 A | 4/1984 | Blitz | |
| 4,449,930 A | * 5/1984 | Huffman | 433/60 |
| 4,449,931 A | 5/1984 | Saito | |
| 4,459,110 A | 7/1984 | Jackson | |
| 4,494,934 A | 1/1985 | Huffman | |
| 4,521,188 A | 6/1985 | Metzler | |
| 4,533,323 A | 8/1985 | Huffman | |

(Continued)

FOREIGN PATENT DOCUMENTS

| | | |
|---|---|---|
| DE | 34 36 094 | 3/1985 |
| DE | 35 05 680 | 7/1985 |
| DE | 35 21 137 | 12/1986 |
| DE | 38 25 014 | 1/1990 |
| EP | 0 151 086 | 8/1985 |
| EP | 0 210 484 | 2/1987 |
| EP | 0 277 026 A2 | 8/1988 |
| EP | 0 291 821 | 11/1988 |
| EP | 0 528 335 | 2/1993 |
| FR | 2 750 851 A1 | 1/1998 |
| GB | 866118 | 4/1961 |
| WO | WO 88/10101 | 12/1988 |

*Primary Examiner*—Nicholas D. Lucchesi
(74) *Attorney, Agent, or Firm*—Merchant & Gould P.C.

(57) ABSTRACT

A premanufactured dental model base, and method, for supporting a cast dental model. The dental model base may be selectively connected to an articulator attachment plate which is adaptable for connecting the dental model base to a metal articulator. The same dental model base, at a user's option, may also be connected to a disposable articulator through a groove in the base that engages a disposable articulator tongue or by connecting a disposable articulator ball directly to a socket in the base. Thus, the dental model base may be conveniently used with either a metal articulator or a disposable articulator. In one embodiment, a concave socket at one end of the dental model base may engage an articulator ball or may engage the articulator attachment plate such that the attachment plate is detachably connected to the dental model base.

26 Claims, 11 Drawing Sheets

U.S. PATENT DOCUMENTS

| | | |
|---|---|---|
| 4,538,987 A | 9/1985 | Weissman |
| 4,548,581 A | 10/1985 | Huffman |
| 4,608,016 A | 8/1986 | Zeiser |
| D286,179 S | 10/1986 | Huffman |
| D286,436 S | 10/1986 | Huffman |
| D289,924 S | 5/1987 | Huffman |
| 4,708,648 A | 11/1987 | Weissman |
| 4,708,835 A | 11/1987 | Kiefer |
| 4,721,464 A | 1/1988 | Roden et al. |
| 4,734,033 A | 3/1988 | Huffman |
| 4,767,330 A | 8/1988 | Burger |
| 4,767,331 A | 8/1988 | Hoe |
| 4,786,253 A * | 11/1988 | Morais .................. 433/60 |
| 4,842,242 A * | 6/1989 | Huffman ............. 433/60 X |
| D302,725 S | 8/1989 | Huffman |
| D305,361 S | 1/1990 | Huffman |
| D305,362 S | 1/1990 | Huffman |
| D306,206 S | 2/1990 | Huffman |
| 4,898,359 A | 2/1990 | Gopon |
| 5,028,235 A | 7/1991 | Smith |
| 5,049,075 A | 9/1991 | Barrut |
| 5,098,290 A | 3/1992 | Honstein et al. |
| 5,100,317 A * | 3/1992 | Darnand .................. 433/60 |
| 5,197,874 A | 3/1993 | Silva et al. |
| 5,207,574 A | 5/1993 | Garland |
| 5,352,117 A | 10/1994 | Silva |
| 5,393,227 A | 2/1995 | Nooning |
| 5,466,152 A | 11/1995 | Walter |
| 5,766,007 A | 6/1998 | Huffman |
| 5,769,634 A | 6/1998 | Choi |
| 5,788,489 A | 8/1998 | Huffman |
| 5,800,166 A | 9/1998 | Huffman |
| 5,868,569 A | 2/1999 | Huffman |

* cited by examiner

DENTAL MODEL BASE ASSEMBLY

BACKGROUND OF THE INVENTION

This invention relates generally to a dental model base assembly and more particularly to such an assembly in which a premanufactured dental base may, at the option of a technician, be attached either to a disposable dental articulator or to a metal articulator.

Damaged teeth may be repaired or replaced by crowns, bridge inlays or other common dental prosthesis. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity.

The model is typically formed by having a patient bite into a pliant casting material which cures to create a mold cavity having a negative impression of the patient's teeth and gums. The mold can be of all or any portion of the patient's gum line. A castable material is then poured into the negative impression to create a stone replica or dental model of the patient's teeth and gums.

To facilitate prosthesis development, the replica of the damaged tooth or teeth is severed from the remainder of the dental model. In one prior art system, severability is achieved by positioning the knurled end of a tapered dowel pin in the uncured stone material in correspondence with the damaged tooth or teeth. The dowel pin or pins must be carefully aligned and held in position which requires skill and time. Once the casting of the gum and teeth has hardened, the cured dental model is positioned adjacent an uncured dental model base which is held in a dental base mold. The tapered portion of the dowel pins protruding from the dental model are positioned in the uncured dental model base. To prevent bonding of the damaged tooth model with the dental model base, wax may be placed between the base and the dental model and around the tapered portion of the dowel pins associated with the damaged tooth model.

Once the dental model base has cured, a saw cut on each side of the damaged tooth model is made down to the dental model base which allows removal of the damaged tooth model and the attached dowel from the rest of the dental model.

After the damaged tooth model is removed, the prosthesis can be fitted and adjusted without the spacial limitations encountered when the damaged tooth model is joined to the full dental model. After the prosthesis is made and attached to the dental model segment, the tapered dowel attached to the dental model segment is guided into its respective aperture in the dental model base which guides the dental model segment to its position in the dental model. Alignment and visual conformity are then assessed.

Alignment is ascertained by evaluating the registration of the repaired tooth with the dental model of the patient's opposing teeth. This is achieved by connecting the upper and lower dental model to an articulator. If the prosthesis is out of alignment or does not visually conform to the rest of the patient's teeth, the dental model segment containing the damaged tooth can be removed, adjusted and returned to the dental model base. This process is repeated until proper alignment and visual conformity is achieved. Thus, the model of the damaged tooth may be removed and inserted into the base repeatedly. This repeated removal and reinsertion can damage the fit of the tapered portion of the dowel pin within the cast dental model base which decreases the accuracy of the alignment procedure.

Several plastic dental model bases exist. Examples are described in U.S. Pat. No. 5,788,489. These plastic bases facilitate mounting a cast dental model and overcome some of the difficulties inherent in cast dental model bases. However, plastic bases must also be attached to articulators.

The Vertex® articulator is one disposable articulator typically used to check the alignment of repaired teeth. The Vertex® articulator has a ball and socket joint that permits alignment of the articulator with dental model bases supporting a variety of different dental models. The Vertex® articulator socket member is formed with a tongue opposite the socket. The tongue is typically glued to a slot in the rear portion of the cast dental model bases. The Vertex® articulator may also be glued to slots formed in plastic dental model bases. An example is depicted in FIG. 9 of U.S. Pat. No. 5,788,489.

Other common articulators are metal and the dental model is attached semi-permanently by applying a bonding agent, such as plaster, to the dental model base and the articulator. An example is depicted in FIG. 15 of U.S. Pat. No. 5,788,489. While metal articulators may be separated at the hinge, protruding portions of the articulator obstruct access to the dental model from certain directions. A technician may prefer using one type of articulator in certain circumstances and the other when the circumstances are different.

SUMMARY OF THE INVENTION

The present invention is directed to a significant improvement to the invention disclosed in U.S. Pat. No. 5,788,489. This invention provides the technician with a unique dental model base assembly that can be used with a variety of articulators types. Thus, increasing the accuracy of the adjustment of the dental model.

In one embodiment of the invention a premanufactured dental model base includes a dental model base body with a dental model support surface. The base body has a wall extending from the dental model support surface. The base body has a first end and a second end, and one of the ends has a socket adapted to engage a ball.

Another embodiment includes a dental model kit that includes, a dental model base that has a socket at a first end and a dental model base coupling at a second end, and an articulator attachment plate. The articulator attachment plate has a ball connected to an attachment plate first end and an attachment plate coupling at an attachment plate second end. The attachment plate coupling is adapted to engage the dental model base coupling. The ball is adapted to slidably engage the socket.

Another embodiment includes a dental model base assembly that includes a dental model base body with a spherical concavity in a first end and a base body connector at a second end and an attachment plate. The attachment plate is disengably connected to the dental model base body connector. The attachment plate has a spherical convex element for engaging the spherical concavity.

Another embodiment includes a method comprising the steps of slidingly engaging a ball at a first end of an attachment plate with a socket at a first end of a dental model base. The next step is pivoting the attachment plate relative to the dental model base about the ball and socket. The next step is slidingly engaging a connector on the attachment plate with a receiver at the base body second end where the sliding engagement creates a bias between the ball and the connector. The final step is fully engaging the connector with the receiver such that the attachment plate is securely and detachably connected to the dental model base.

Another embodiment includes a premanufactured dental model base that includes dental model base body that has a molar end and an incisor end opposite the molar end. The molar end has a spherical socket sized and positioned to detachably engage a round portion of an articulator attachment plate or to fixedly connect to a round portion of an articulator.

Another embodiment includes a premanufactured dental model base that includes a dental model support surface and a plurality of tapered pins protruding from the support surface. The pins being of the same material as the base and are formed with the base. A wall adjacent the dental model support surface the wall having a round depression at one end of the dental model base.

Another embodiment includes dental model base that includes a dental model support surface that has a first end and a wall adjacent the dental model support surface. The wall has a socket formed adjacent the dental model support surface first end. The socket being engagably at a user's option with either a ball connected to an articulator or with a round portion of an articulator attachment plate Another embodiment includes an articulator attachment plate that includes an articulator attachment side. The articulator attachment side has plaster retaining protrusions, a dental model side opposite the articulator attachment side, a first and second end, a ball supporting member extending from the dental model side at the first end, a round protrusion extending from the ball supporting member remote from the dental model side, and a hook extending from the dental model attachment side at the second end.

Another embodiment includes a premanufactured dental model base that includes a dental model base body that has a dental model support surface. The base body has a wall extending from the dental model support surface. The base body has a first end and a second end. One of the ends has a ball adapted to engage a socket.

Another embodiment includes a full arch dental model base that includes a dental model support surface. The dental model support surface has an outer perimeter generally following the curvature of a patient's gum, a first end of the support surface corresponding generally to the location of incisors on the gum, and a wall extending from the support surface. The wall being generally perpendicular to the support surface. A connector at the first end of the dental model base. The dental model has a second end remote from the first end. The second end has a first side and a second side. A first concavity at the second end first side and a second concavity at the second end second side. An articulator attachment bar is interposed between the second end first side and the second end second side. The articulator attachment bar has a groove for engaging an articulator tongue.

DETAILED DESCRIPTION OF THE PREFERRED EMBODIMENT

Figure 1:
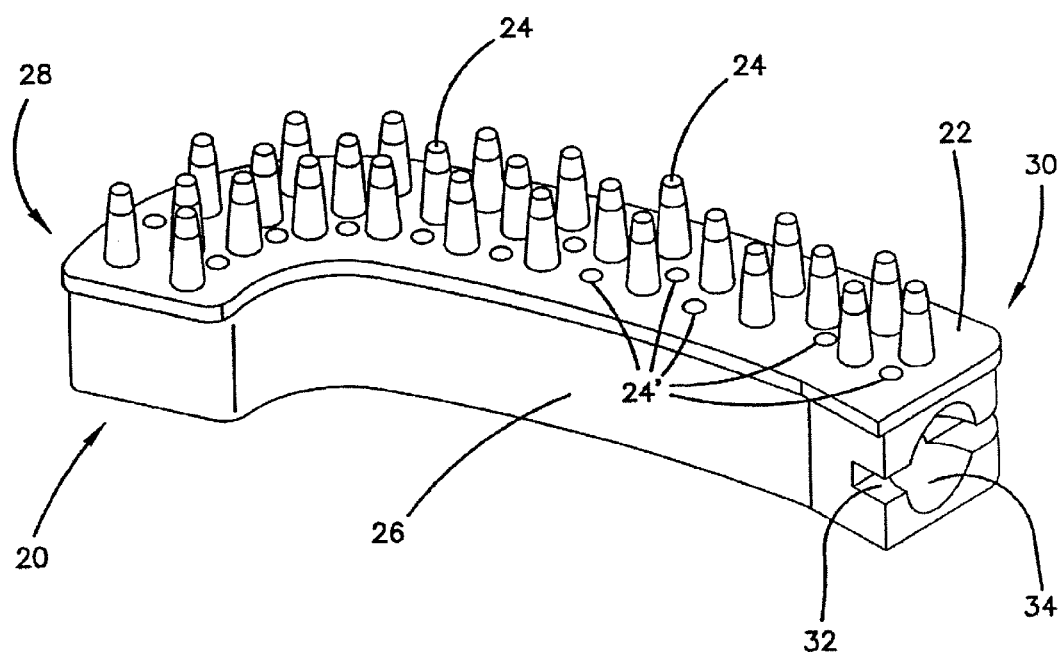
FIG. 1 is a right side, rear and top perspective view of a quadrant dental model base.

FIG. 1 depicts a quadrant dental model base 20 according to one embodiment of the present invention. In this embodiment, a clear acrylic plastic is preferred, however, many other materials may be used. As shown in FIG. 1, the dental model base 20 has a model support surface 22. The shape of the dental model support surface 22 follows the general contours of half of a normal gum.

In this embodiment a plurality of tapered pins 24 are formed with the dental model base 20. The pins 24 are formed of the same material as the base 20 and the base 20 and pins 24 form one integral body. The pins 24 extend from the dental model support surface 22. The pins may releasably engage a cast dental model. The dental model support surface 22 defines apertures 24' extending from the dental model support surface 22 into the dental model. Features of the present invention may be adapted to other premanufactured base designs such as those described in U.S. Pat. Nos. 5,788,4891.

A wall 26 extends from the dental model support surface 22 opposite the pins 24. The wall 26 generally follows the periphery of the dental model support surface 22.

The front 28 of the dental model base 20 is configured to support the front of a dental model. In other words, the pins 24 at the front 28 of the base 20 should align generally with the casting of a patient's incisors.

The rear 30 of the base 20 is configured to support the rear of a dental model. In other words, the pins 24 at the rear 30 of the base 20 should align generally with the casting of the patient's molars.

The rear 30 of the base 20 has an articulator attachment groove 32 formed across a socket 34. The socket 34 defines a hemispheric void.

Figure 2:
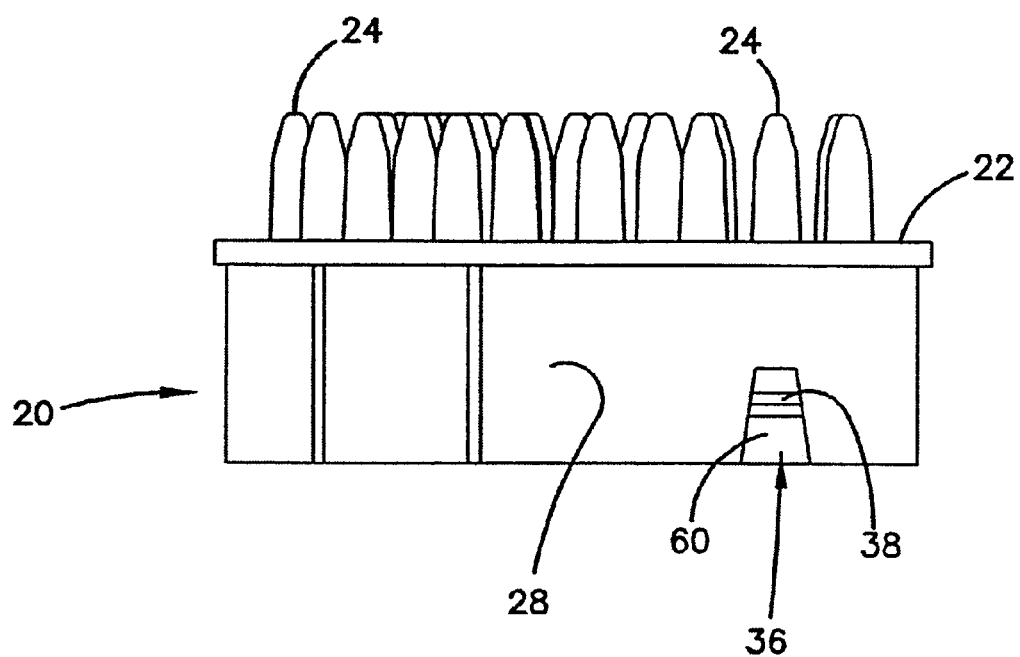
FIG. 2 is a front elevation view of a quadrant dental model base.

As shown in FIG. 2, the front 28 of the base 20 has a recess 36 forming a notch 38.

Figure 3:
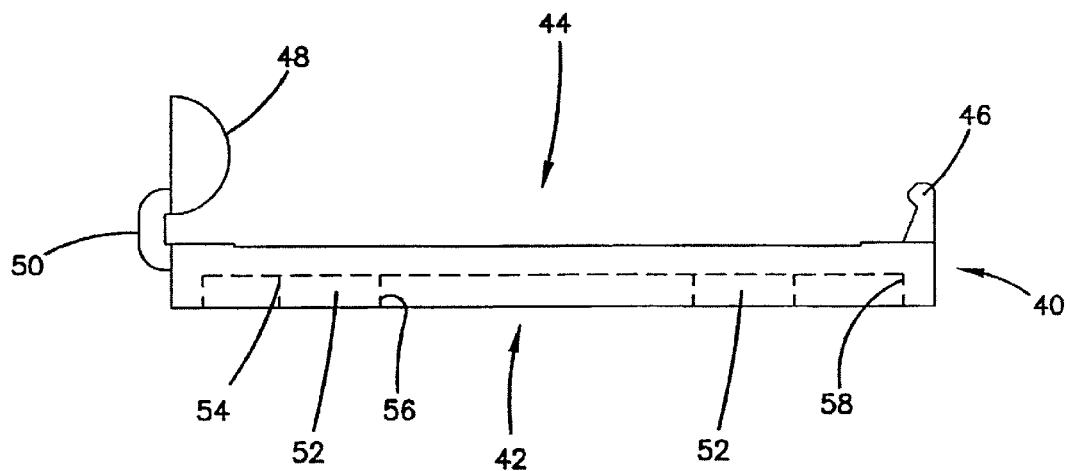
FIG. 3 is a side elevation view of an attachment plate for a quadrant dental model base.
Figure 4:
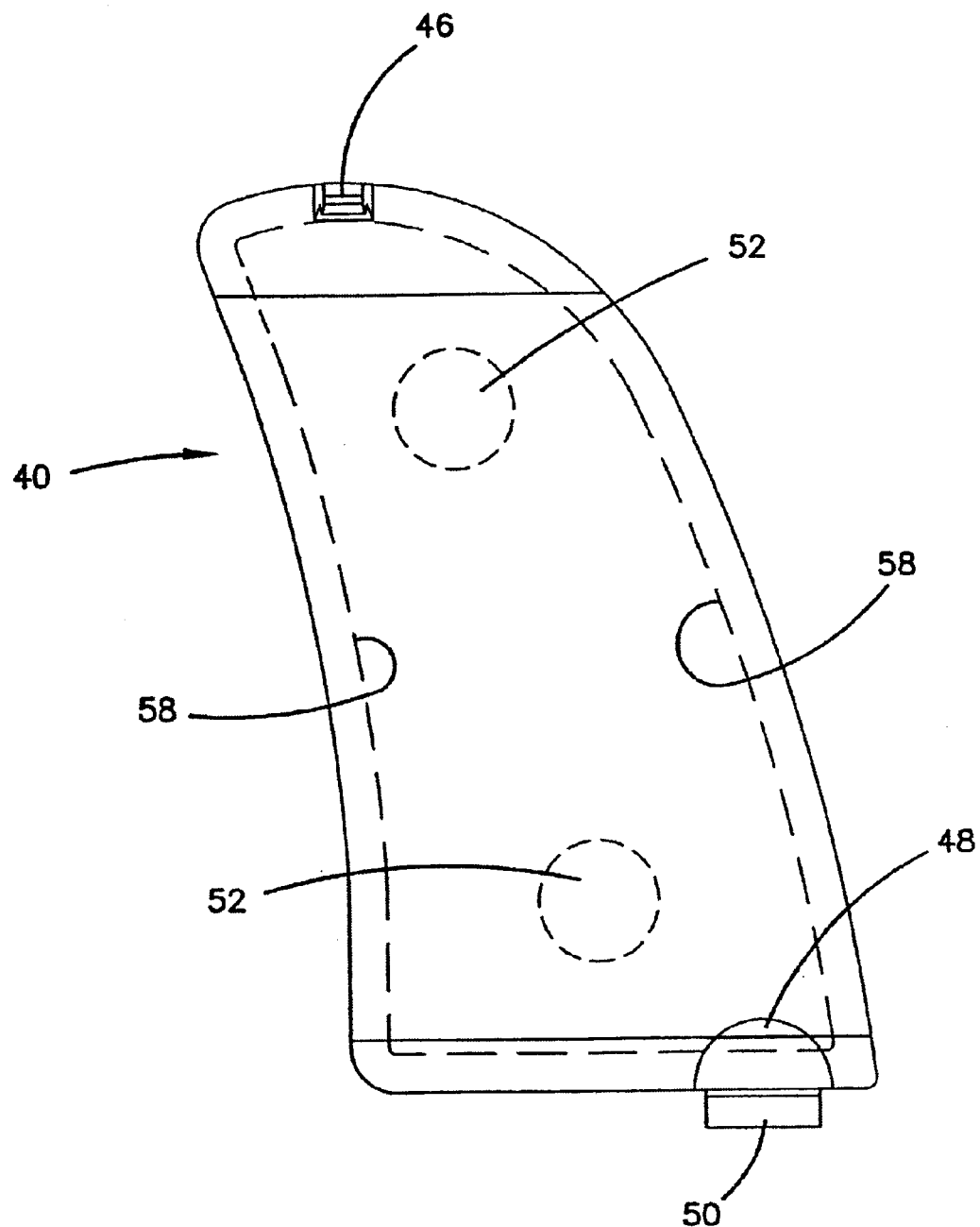
FIG. 4 is a top plan view of an attachment plate for a quadrant dental model base.

FIGS. 3 and 4 show an attachment plate 40. The attachment plate 40 has an articulator attachment side 42 and a base engagement side 44. A hook 46 is at one end of the attachment plate 40. A hemisphere or ball 48 is connected to the opposite end of the attachment plate 40 by a hemisphere connecting member 50.

The attachment plate 40 has two posts 52 positioned in a void on the articulator attachment side 42 of the attachment plate 40. The posts are tapered slightly such that the base of each post 54 has a smaller diameter than the head of the post 56. Also, the walls 58 defining the void on the articulator attachment side 42 of the attachment plate 40 are tapered such that the walls 58 are thicker at the articulator attachment side surface 42 than at the base of the void. The tapered posts 52 and walls 58 aid in securing the attachment plate 40 to a typical metal articulator.

Figure 5:
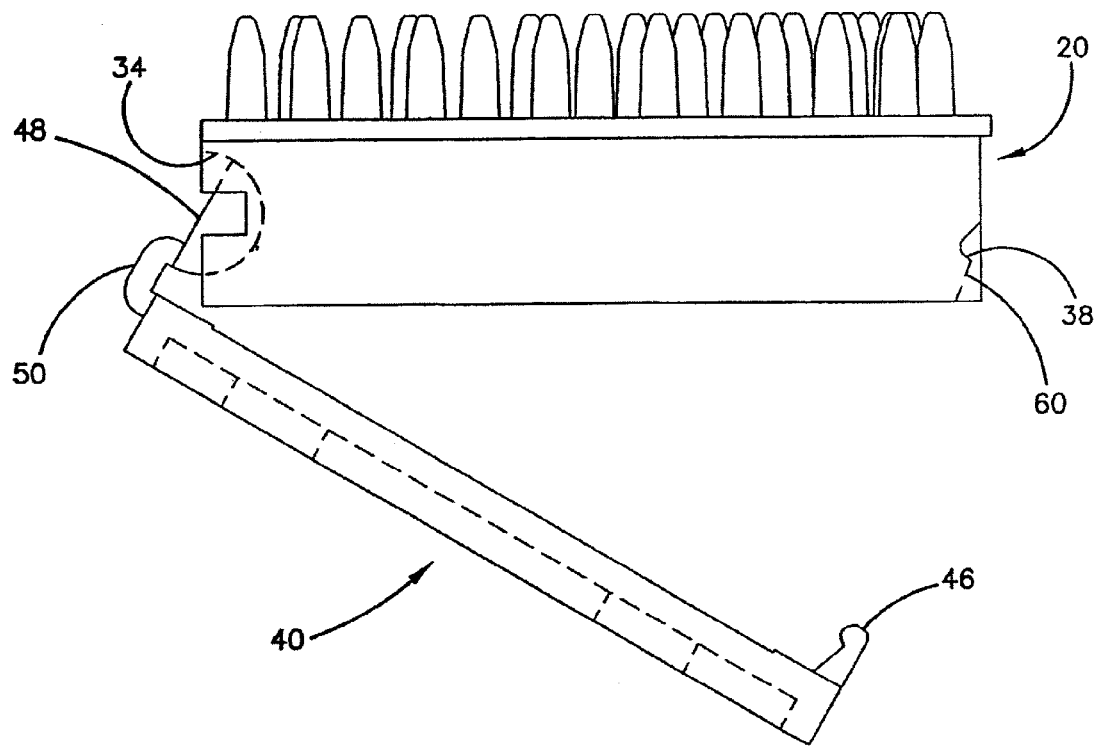
FIG. 5 is a side elevation view of the attachment plate and quadrant dental model base.

The attachment plate 40 is connected to the base 20 by placing the hemisphere or ball 48 in the socket 34 formed in the rear 30 of the base 20, as shown in FIG. 5. The attachment plate 40 is then rotated about the ball 48 and socket 34 relative to the base 20.

Figure 6:
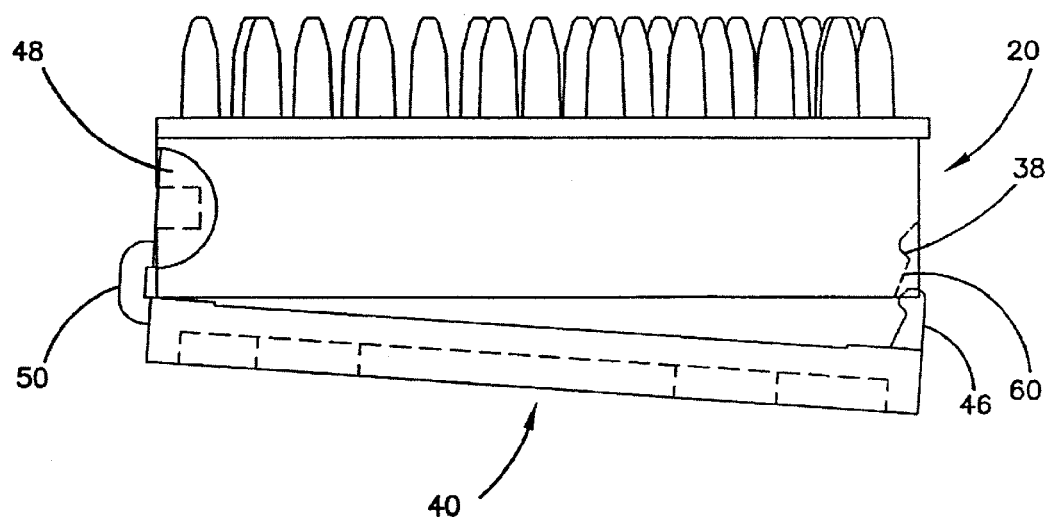
FIG. 6 is a side elevation view of the attachment plate partially engaged with the quadrant dental model base.
Figure 7:
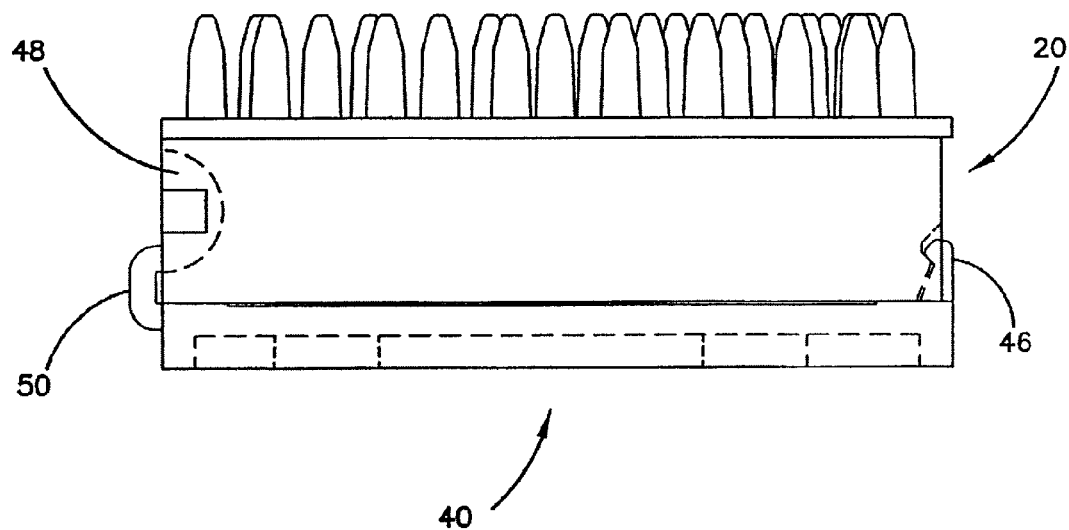
FIG. 7 is a side elevation view of the attachment plate fully engaged with the quadrant dental model base.

As shown in FIG. 6, the hook 46 slidingly engages the recess 36 in the base 20. As pressure is applied to join the base 20 and attachment plate 40, the hook 46 slides along the inclined plane 60 of the recess 36. When the attachment plate 40 is properly engaged with the base 20, as shown in FIG. 7, the hook 46 engages the recess notch 38 and secures the attachment plate 40 to the base 20.

Figure 8:
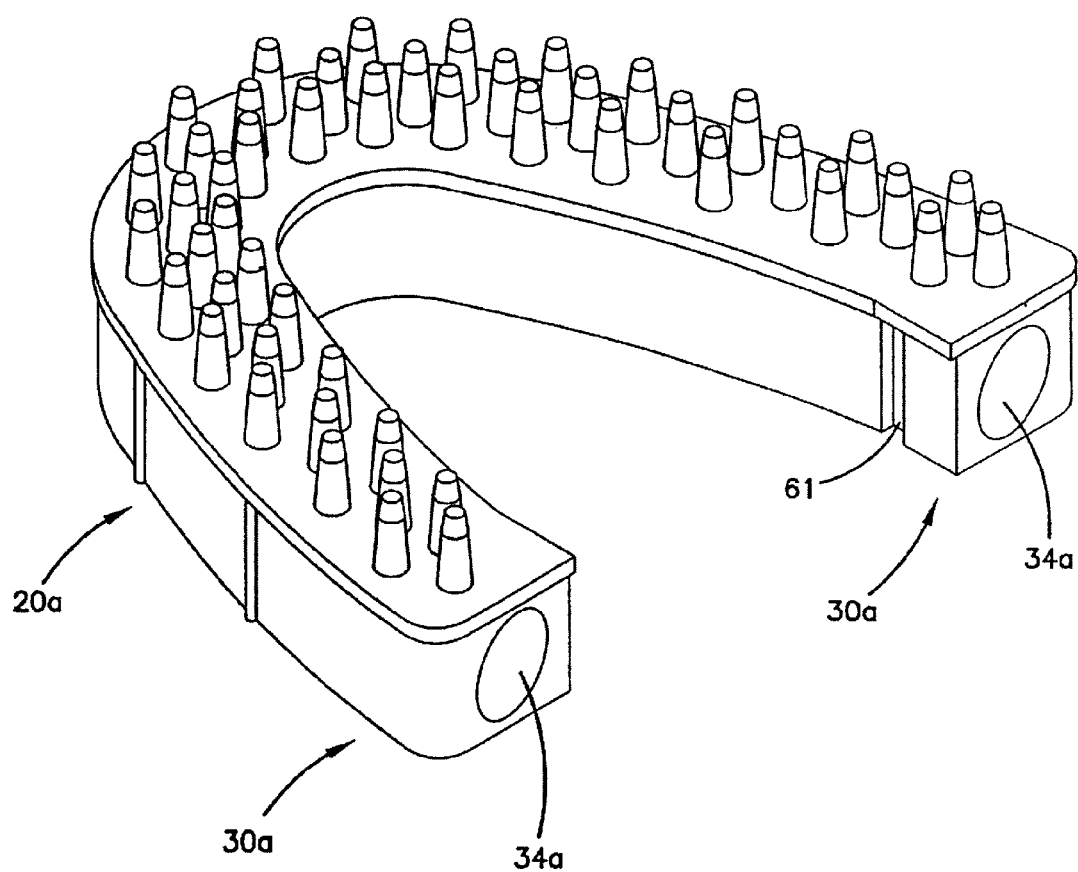
FIG. 8 is a right side, rear and top perspective view of a full arch dental model base.
Figure 9:
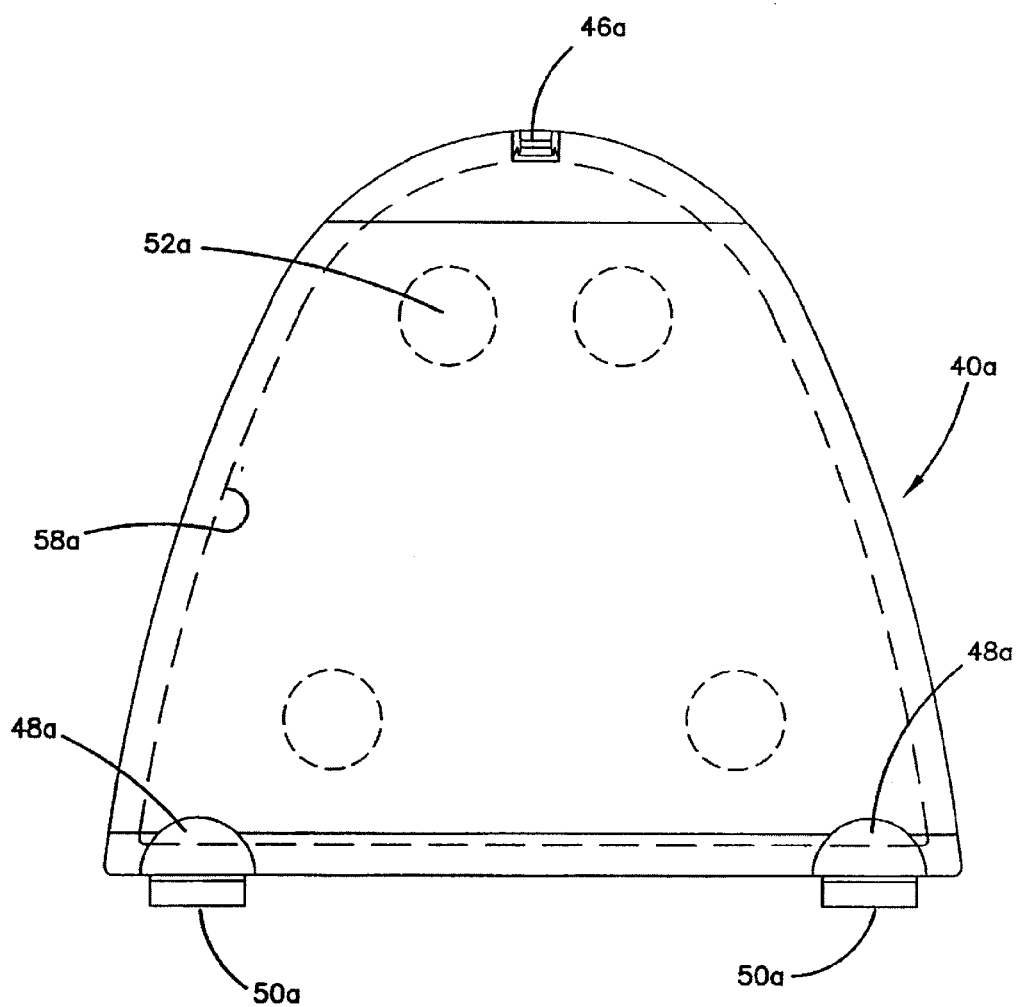
FIG. 9 is a top plan view of an attachment plate for a full arch dental model base.

FIG. 8 depicts a base 20a configured to support a full arch dental model. As shown, the full arch base 20a has two sockets 34a at the rear 30a of the base 20a. FIG. 9 depicts an articulator attachment plate 40a for a full arch dental model base. The attachment plate 40a has tapered posts 52a and tapered walls 58a for securing the plate to a metal articulator. Two hemisphere connecting members 50a connect a pair of hemispheres or balls 48a to the rear of plate 40a. A hook 46a extends from the front of the plate. Two vertical slots 61 are located near the rear of the full arch base 20a.

Figure 10:
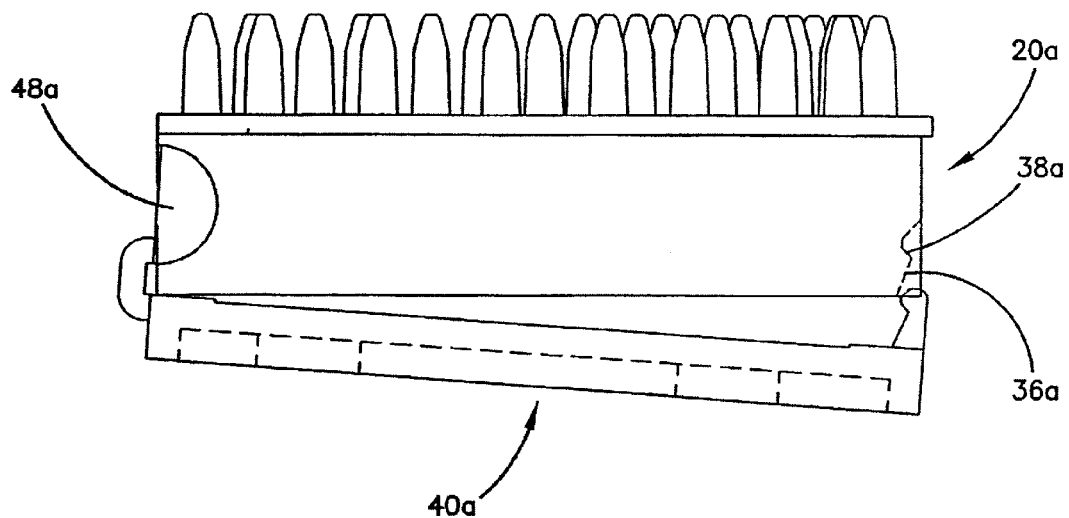
FIG. 10 is a side elevation view of the attachment plate partially engaged with the full arch dental model base.

As depicted in FIG. 10, the full arch base 20a has a recess 36a and notch 38a. A full arch attachment plate 40a is connected to a full arch base 20a by inserting two full arch attachment plate balls 48a into the two full arch base sockets 24a and thereafter preceding as described above.

Figure 11:
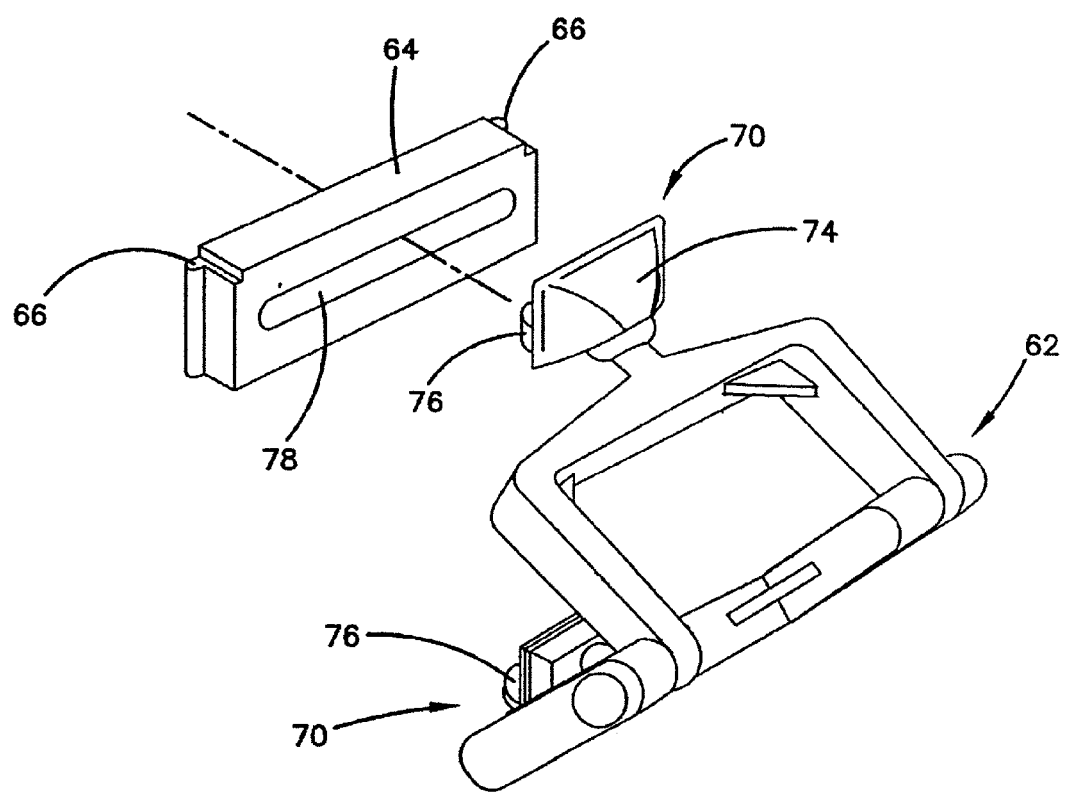
FIG. 11 is a perspective view of a typical disposable articulator used with the invention.

The full arch base 20a may be connected to a disposable articulator 62 by sliding an articulator attachment bar 64 into the vertical slots 61. As shown in FIG. 11, the attachment bar has two flanges 66 that slidingly engage the vertical slots 61. The articulator 62 is defined by a flexible hinge and a pair of ball and socket joints 70. The articulator ball 72 engages an articulator socket 74 which may be attached to a base by inserting an articulator tongue 76 into a groove 78 in an articulator attachment bar 64. It was also known to insert the tongue 76 into a groove in a cast base.

If a technician chooses to use a metal articulator, he or she may connect an articulator attachment plate to a dental model base as described above. Plaster may then be used to secure the plate to the metal articulator.

If the technician chooses to use a disposable articulator, the technician may simply insert the articulator tongue 76 into the groove 32 at the rear of the quadrant base 20. If a full arch base is used, the tongue 76 can be inserted into the articulator attachment bar groove 78 after the attachment bar 64 is fixed to the full arch base 20a.

Alternatively, the technician may remove the disposable articulator socket 74 and place the articulator ball 72 directly in the socket 34 at the rear of the base 20.

The foregoing describes various embodiments of the claimed invention. The claimed inventions are not limited to the embodiments described above. For example, it is contemplated that the principles of the invention described above can be applied to numerous different dental model base designs. It is also contemplated that a socket could be formed in a disposable articulator that would engage a ball formed at the rear of the dental model base. Numerous other alternative constructions exist that fall within the scope of the claimed invention.

I claim:

1. A premanufactured dental model base comprising:
   a dental model base body, said dental model base body having a dental model support surface;
   said base body having a wall extending from said dental model support surface;
   said base body having a first end and a second end, and one of the said ends having a socket adapted to engage a ball wherein:
   said dental model base body has a slot at one of said ends adapted to engage a disposable articulator.

2. The dental model base of claim 1 wherein: said socket is adapted to engage a ball connected to a disposable articulator.

3. The dental model base of claim 1 wherein: said base body is adapted to engage an articulator attachment plate.

4. The dental model base of claim 3 wherein: said socket is adapted to engage a ball connected to articulator attachment plate.

5. The dental model base of claim 1 wherein:
   a plurality of apertures pass through said dental model support surface and said dental model base.

6. The dental model base of claim 5 wherein:
   said apertures are adapted to engage pins connected to a dental model.

7. The dental model base of claim 5 wherein;
   said apertures are adapted to form stone dowels; and
   said stone dowels formed with said dental model.

8. A premanufactured dental model base comprising:
   a dental model base body, said dental model base body having a dental model support surface;
   said base body having a wall extending from said dental model support surface;
   said base body having a first end and a second end, and one of the said ends having a first socket adapted to engage a ball;
   said dental model support surface is adapted to support a full arch dental model;
   said first end of said dental model base body corresponds to the molar portion of said full arch dental model;
   said first end having a first side corresponding to the left molars on the dental model and a second side corresponding to the right molars on the dental model; and
   said dental model base body having said first socket on said first side of said first end and a second socket on said second side of said first end.

9. The dental model base of claim 8 further comprising:
   an articulator attachment bar;
   said articulator attached bar interposed between said dental model base body first end first side and said dental model base body first end second side.

10. The dental model base of claim 9 wherein: said attachment bar is slidingly engageable with said dental model base body.

11. The premanufactured dental model base of claim 8 wherein: one of said sockets are adapted to engage an articulator attachment plate.

12. A dental model kit comprising:
    a dental model base;
    said dental model base having a socket at a first end and a dental model base coupling at a second end; and an articulator attachment plate;
    said articulator attachment plate having a ball connected to an attachment plate first end and an attachment plate coupling at an attachment plate second end wherein said attachment plate coupling is adapted to engage said dental model base coupling and said ball is adapted to slidably engage said socket.

13. The dental model kit of claim 12 further comprising: an articulator attachment bar.

14. The dental model kit of claim 12 further comprising a disposable articulator.

15. A dental model base assembly comprising:
a dental model base body, said dental model base body having spherical concavity in a first end and a base body connector at a second end; and
an attachment plate;
said attachment plate disengably connected to said dental model base body connector;
said attachment plate having a spherical convex element engaging said spherical concavity.

16. The dental model assembly of claim 15 wherein:
said spherical convex element is biased to secure said attachment plate to said dental model base body.

17. A method comprising the steps of:
slidingly engaging a ball at a first end of an attachment plate with a socket at a first end of a dental model base;
pivoting said attachment plate relative to said dental model base about said ball and socket;
slidingly engaging a connector on said attachment plate with a receiver at said base body second end wherein said sliding engagement creates a bias between said ball and said connector; and
fully engaging said connector with said receiver such that said attachment plate is securely and detachably connected to said dental model base.

18. The method of claim 17 wherein:
said full engagement of said connector with said receiver releases a portion of said bias.

19. The method of claim 17 wherein:
said engagement releases substantially all of said bias.

20. The method of claim 17 additionally comprises the step of connecting said articulator attachment plate to an articulator.

21. A premanufactured dental model base comprising:
a dental model base body;
said dental model base body having a molar end and an incisor end opposite said molar end;
said molar end having a spherical socket sized end positioned to detachably engage a round portion of an articulator attachment plate or to fixedly connect a round portion of an articulator;
said base has a slot at said molar end; and
said slot sized and positioned to receive a tongue connected to an articulator.

22. A premanufactured dental model base comprising:
a dental model support surface;
a plurality of tapered pins protruding from said support surface;
said pins being of the same material as said base, said pins formed with said base; and
a wall adjacent said dental model support surface said wall having a round depression at one end of said dental model base.

23. The premanufactured dental model base of claim 22 wherein:
said round depression is a socket;
said dental model base has a second end remote from said first end; and
said dental model base has a receiver at said second end.

24. An articulator attachment plate comprising:
an articulator attachment side, said articulator attachment side having plaster retaining protrusions;
a dental model side opposite said articulator attachment side;
a first and second end;
a ball supporting member extending from said dental model side at said first end;
a round protrusion extending from said ball supporting member remote from said dental model side; and
a hook extending from said dental model attachment side at said second end.

25. A full arch dental model base comprising:
a dental model support surface;
said dental model support surface having an outer perimeter generally following the curvature of a patient's gum;
a first end of said support surface corresponding generally to the location of incisors on said gum;
a wall extending from said support surface, said wall being generally perpendicular to said support surface;
a connector at said first end of said dental model base;
said dental model having a second end remote from said first end, said second end having a first side and a second side;
a first concavity at said second end first side and a second concavity at said second end second side;
an articulator attachment bar interposed between said second end first side and said second end second side said articulator attachment bar having a groove for engaging an articulator tongue.

26. A method of connecting a dental model base to an articulator attachment plate comprising:
(a) providing a dental model base having a dental model base body, the dental model base body comprising:
(i) a dental model support surface;
(ii) a wall extending from the dental model base support surface; and
(iii) a first end and a second end, one of said ends having a socket adapted to engage a ball attached to an articulator attachment plate;
(b) providing an articulator attachment plate having a ball; and
(c) connecting the articulator attachment plate to the dental model base by placing the ball of the articulator attachment plate in the socket of the dental model base body.

* * * * *